US00PP27374P3

(12) United States Plant Patent
Robacker et al.

(10) Patent No.: US PP27,374 P3
(45) Date of Patent: Nov. 15, 2016

(54) ***VITEX AGNUS-CASTUS* PLANT NAMED 'V07-SC-OP-4'**

(50) Latin Name: *Vitex agnus-castus*
Varietal Denomination: V07-SC-OP-4

(71) Applicant: University of Georgia Research Foundation, Inc., Athens, GA (US)

(72) Inventors: Carol D. Robacker, Peachtree City, GA (US); David A. Knauft, Watkinsville, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 99 days.

(21) Appl. No.: 14/121,983

(22) Filed: Nov. 10, 2014

(65) Prior Publication Data

US 2016/0135347 P1 May 12, 2016

(51) Int. Cl.
*A01H 5/02* (2006.01)

(52) U.S. Cl.
USPC ..... Plt./226

(58) Field of Classification Search
USPC ..... Plt./226, 216
See application file for complete search history.

*Primary Examiner* — June Hwu
(74) *Attorney, Agent, or Firm* — Klarquist Sparkman, LLP

(57) ABSTRACT

A *Vitex agnus-castus* plant named 'V07-SC-OP-4' has short, dense panicles and dark pink flowers.

4 Drawing Sheets

Genus and species: *Vitex agnus-castus*.

Varietal denomination: The new *Vitex agnus-castus* claimed is of the cultivar denominated 'V07-SC-OP-4'.

BACKGROUND OF THE INVENTION

The present invention relates to a new and distinct cultivar of *Vitex agnus-castus* hereinafter referred to by the varietal domination 'V07-SC-OP-4'.

Pedigree and history: Under the direction of David Knauft, seeds from *Vitex agnus-castus* 'Shoal Creek' (unpatented) were irradiated with 4kr gamma radiation in 2006. These seeds were planted in Watkinsville, Ga. in 2007; a selection was made and labeled 'SC4-01-07' (unpatented). This selection was allowed to open-pollinate, and the resulting seeds were sown in 2008. Twelve seedlings germinated, and were transferred to Carol Robacker's breeding program in Griffin, Ga. in 2009. These 12 plants were transplanted into a field plot in Griffin, Ga. in June 2009. One of these plants was selected for its dark pink flowers and was labeled 'V07-SC-OP-4'. This plant has been evaluated for four winters and five summers. Asexually propagated progeny, grown from stem cuttings, planted in 2009 in Griffin, Ga. have also been observed. Height and width data has been collected annually. Cold damage was assessed each spring.

Mean panicle lengths and number of panicles per compound panicle were counted each summer. First bloom and re-bloom dates were noted each year. Data was collected on leaf yellowing, leaf drop, thinning, and leaf spot in July, August and September of each year.

'V07-SC-OP-4' plants have been grown for evaluation in an irrigated field plot in Griffin, Ga. These plants have been fertilized annually in the spring. Height after five summer's growth is 335 cm. Stems are R.H.S. (Royal Horticultural Society, 2001) grey-brown N199A or greyed-green 197A when older, round, and covered in tiny curved hairs with scattered longer curved hairs. The trunk color is a mix of greyed-white 156A and grey-brown 199D. Cracking and exfoliation of the trunk or large stems is noticeable at about 5 cm diameter.

Leaves emerge with yellow-green 146A upper surface, changing to a deeper green 137A during the summer, and becoming yellow-green 147A in the fall. Lower leaf surface is greyed-green 191B throughout the season. Leaves are palmately-compound, typically 13 cm×14 cm, with mostly seven leaflets. Margins are entire, with acute apices and bases. The upper leaf surface has many scattered hairs, slightly glandular, while the lower surface is more densely pubescent and very glandular. Leaves are slightly waxy above, dull underneath. Venation is simple. Leaf arrangement on stems is opposite.

Flower buds are red-purple 65C. Flowers occur in an elongated compound panicle, 14 cm long by 3 cm in diameter. At emergence and through full bloom and fading, flowers are red-purple 63C with a darker red-purple N66C splotch on the anterior lip. The peduncle is grayed-green 193D. The number of individual flowers per inflorescence ranges from 242 on the secondary peduncles to 588 on the main stem of the panicle. Sepals are grayed-green 193A with purple-violet N81C streaking.

SUMMARY OF THE INVENTION

'V07-SC-OP-4' plants have been evaluated for four winters and five summers at the Griffin, Ga. site. Height and width data has been collected annually. Cold damage was assessed each spring. Mean panicle lengths and number of panicles per compound panicle were counted each summer. First bloom and re-bloom dates were noted each year. Data was collected on leaf yellowing, leaf drop, thinning, and leaf spot in July, August and September of each year.

'V07-SC-OP-4' was planted into a field plot in Griffin, Ga. in June 2009, while 'Salinas Pink' (unpatented) was planted into the same plot in June 2011. At time of field planting, plants were rooted liners grown in one-gallon containers.

The following characteristics have been consistently observed in the original plant of this new variety and in asexually propagated progeny grown from cuttings and, to the best knowledge of the inventors, their combination forms the unique characteristics of 'V07-SC-OP-4' as a new and distinct cultivar. Asexual propagation by cuttings has proven that these characteristics are firmly fixed in succeeding asexually propagated generations:

1. Short, dense panicles (Table 5; FIGS. 1 and 2);
2. Dark pink flower (FIGS. 3 and 4).

'V07-SC-OP-4' is an improved pink *Vitex* as compared to the industry standard 'Salinas Pink', the only commonly available pink *Vitex*. 'Salinas Pink' is the closest variety known by the inventors to the new cultivator 'V07-SC-OP-4'.

Comparison: Height and width were measured annually. 'Salinas Pink' is similar in size to 'V07-SC-OP-4' (Table 1).

'V07-SC-OP-4' begins blooming about one week later than 'Salinas Pink' each year (Table 2). Both have moderate repeat blooming during summer and fall (Table 3). Panicles on 'Salinas Pink' are much longer than 'V07-SC-OP-4', but both have similar diameter. (Table 4, FIGS. 1, 2). However, the flowers are much closer together along the rachis of the panicles of 'V07-SC-OP-4' compared to 'Salinas Pink', creating a panicle that is fuller (has more flowers per linear length) (Table 5, FIGS. 1, 2). Flowers of 'V07-SC-OP-4' are a darker red-purple (63C) than those of 'Salinas Pink', which are a lighter purple (75C) (FIG. 2). In addition, 'V07-SC-OP-4' has a notable darker red-purple (N66C) blotch on the anterior lip. The forms of both 'V07-SC-OP-4' and 'Salinas Pink' are similar (FIG. 3). A photo of 'V07-SC-OP-4' is shown in FIG. 4.

In comparison to its parent 'Shoal Creek', 'V07-SC-OP-4' has flowers that are a different color and panicles that are of a different size. At peak bloom, 'V07-SC-OP-4' has red-purple 63C flowers with red-purple N66C on their anterior lips, while 'Shoal Creek' has violet N88B flowers with violet-blue N90D on their anterior lips. The panicle length of 'V07-SC-OP-4' is on average 13.9 cm and the diameter is 3.2 cm. The 'Shoal Creek' panicles are larger, with a mean panicle length of 24.1 cm and a diameter of 3.8 cm. 'V07-SC-OP-4' has one long and two to four short subpanicles per panicle, while 'Shoal Creek' has one long and three to six short subpanicles per panicle.

*Vitex agnus-castus* is a deciduous shrub or small tree used in landscapes. This drought tolerant plant may be grown in cold hardiness zones 6 through 9. During cold winters in zone 6, it may die back to the ground, but will likely re-grow from the roots and produce a flowering shrub during the following summer, as flower buds are formed on new growth. Late spring freezes in zone 7 may also cause cold damage and dieback, but the plants recover and bloom during the summer.

'V07-SC-OP-4' has been and is propagated vegetatively by stem cuttings.

TABLE 1

Height and width (cm) of 'V07-SC-OP-4' and 'Salinas Pink' one, two and three years after planting in a field plot in Griffin, Georgia.

| Entry | Year 1 | Year 2 | Year 3 |
|---|---|---|---|
| 'V07-SC-OP-4' | 175 H × 240 W | 235 H × 288 W | 330 H × 362 W |
| 'Salinas Pink' | 118 H × 142 W | 228 H × 291 W | 297 H × 370 W |

TABLE 2

First bloom dates of 'V07-SC-OP-4' and 'Salinas Pink' grown in Griffin, Georgia.

| Entry | First bloom 2011 | First bloom 2012 | First bloom 2013 |
|---|---|---|---|
| 'V07-SC-OP-4' | 5-30 | 5-21 | 6-17 |
| 'Salinas Pink' | — | 5-14 | 6-10 |

TABLE 3

Repeat flowering in July, August, September, and October in 2011, 2012, and 2013.

| Entry | Year | July | August | September | October |
|---|---|---|---|---|---|
| -'V07-SC-OP-4' | 2011 | 1* | 1 | 3 | 0 |
| | 2012 | 0 | 0 | 4 | 2.5 |
| | 2013 | 3 | 0 | 3 | 1 |
| 'Salinas Pink' | 2011 | 0 | 1 | 3 | 2 |
| | 2012 | 2 | 3 | 3 | 2 |
| | 2013 | 1 | 0 | 0.5 | 0.5 |

*Repeat flowering was rated using the following scale: 0 = no flowering; 1 = 10% full bloom; 2 = 20 to 30% full bloom; 3 = 40 to 50% full bloom; 4 = at least 60% full bloom.

TABLE 4

Panicle length, diameter and number of secondary peduncles per panicle averaged over 2011, 2012, and 2013. Measurements were made on four typical or average-sized panicles per plant per year.

| Entry | Mean Panicle length (cm) | Mean Panicle diameter (cm) | Number of secondary peduncles/panicle |
|---|---|---|---|
| 'V07-SC-OP-4' | 14 | 3.1 | Two to four |
| 'Salinas Pink' | 24.1 | 3.2 | Two to four |

TABLE 5

Distance (mm) between pedicels on the rachis of the main panicle and secondary sub-panicles. Measurements were made on four typical panicles.

| Entry | Distance between pedicels on the rachis* | Distance between pedicels on the rachis of the secondary peduncles* | Distance between the bottom two secondary peduncles of the panicle |
|---|---|---|---|
| 'V07-SC-OP-4' | 11.2 | 5.1 | 55.4 |
| 'Salinas Pink' | 23.0 | 13.5 | 60.1 |

*Measurements were made between the second and third pedicels from the bottom of the sub-panicles.

BRIEF DESCRIPTION OF THE FIGURES

The accompanying colored photographic illustrations show the overall appearance and distinct characteristics of the new cultivar of *Vitex agnus-castus*. The colors in the photographs are as close as possible with the photographic and printing technology utilized.

DETAILED BOTANICAL DESCRIPTION

Figure 1:
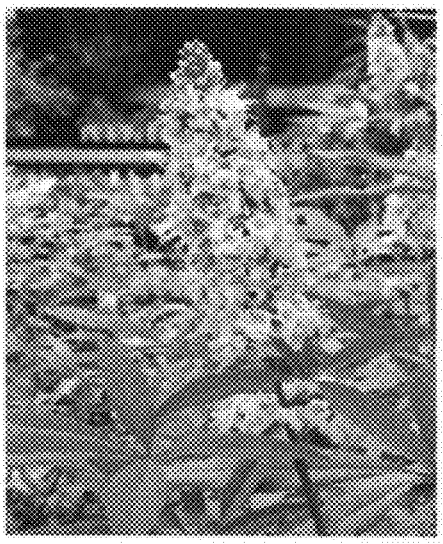
FIG. 1 is a photograph of the new variety 'V07-SC-OP-4' (left image) during flowering and a photograph of 'Salinas Pink' (right image). 'V07-SC-OP-4' has darker pink flowers than 'Salinas Pink'. While 'Salinas Pink' has longer panicles, the flowers on the panicles of 'V07-SC-OP-4' are closer together and larger, creating a fuller, more floriferous appearance.
Figure 1:
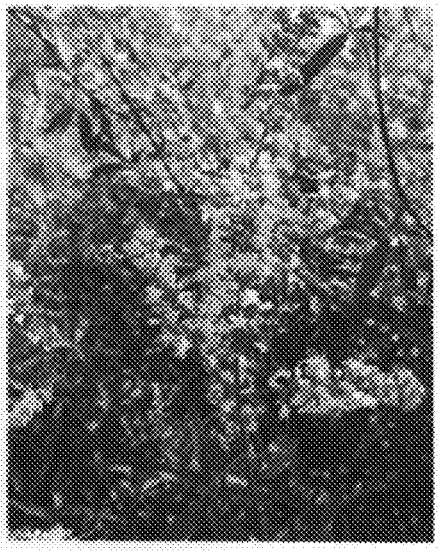
Figure 2:
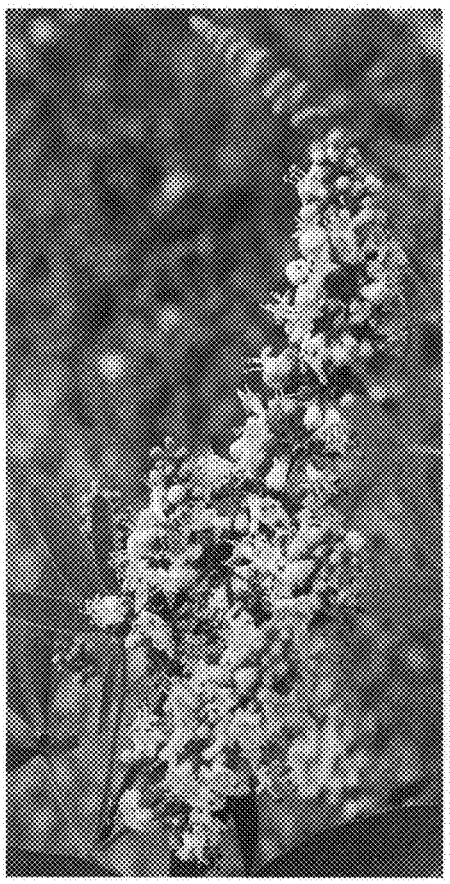
FIG. 2 is a photograph of 'V07-SC-OP-4' (left image), which has flowers that are darker pink and closer together along the rachis than those of 'Salinas Pink' (right image).
Figure 2:
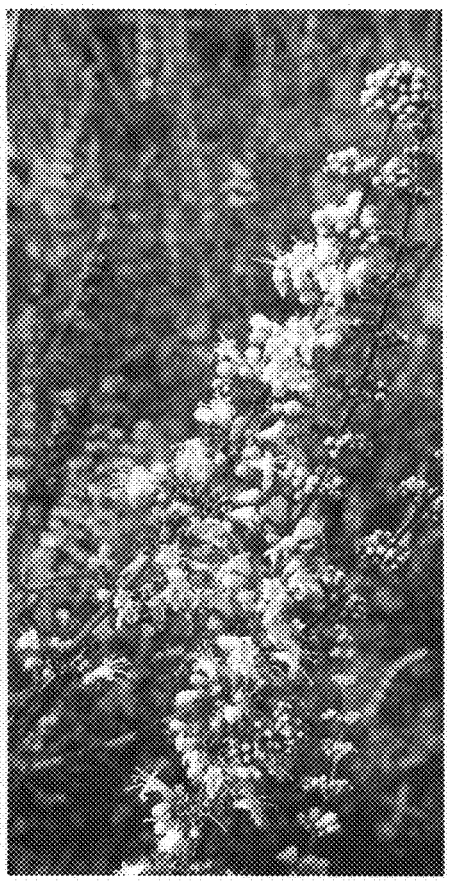
Figure 3:
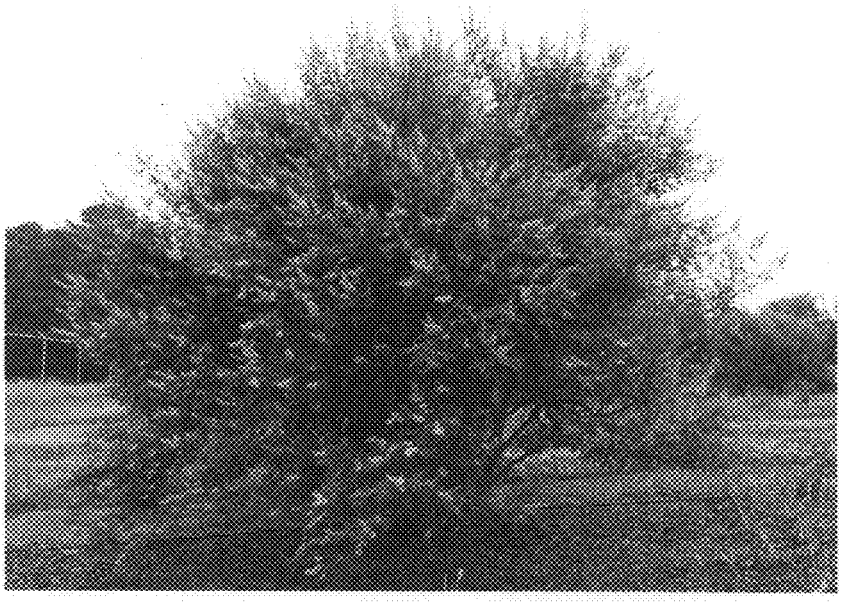
FIG. 3 is a photograph of 'V07-SC-OP-4' (top image) and 'Salinas Pink' (bottom image) at peak bloom. In this photo, 'V07-SC-OP-4' had been in a field plot for five years and 'Salinas Pink' had been in the same plot for three years.
Figure 3:
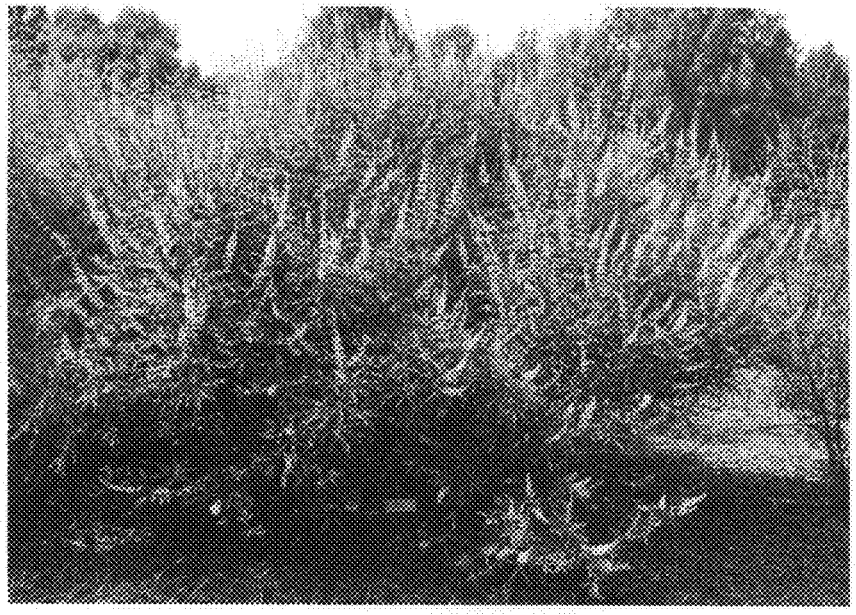
Figure 4:
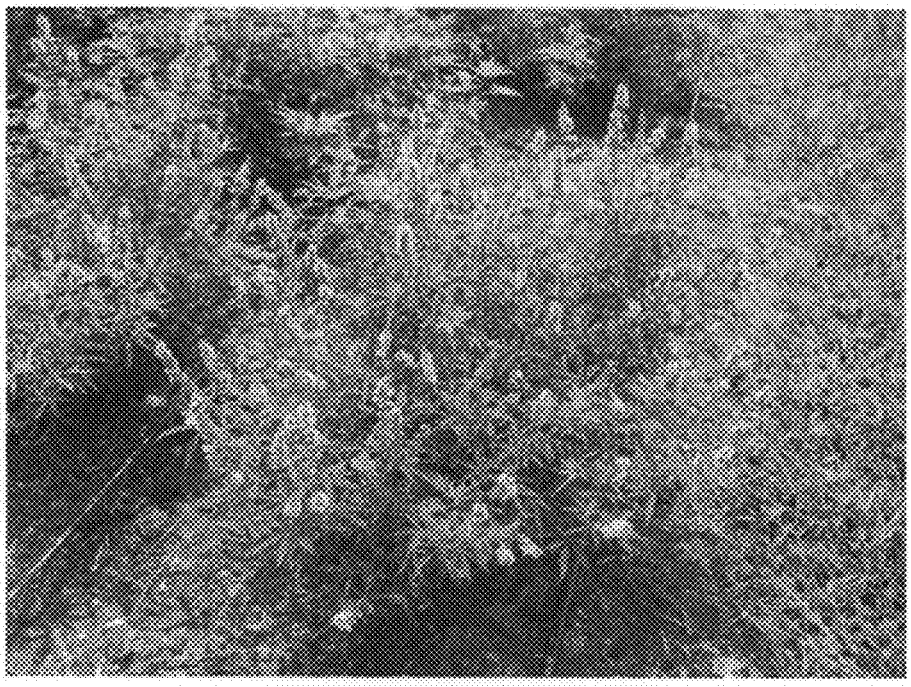
FIG. 4 is a photograph of 'V07-SC-OP-4' growing in plant trials in West Grove, Pa.

The following is a detailed description of the *Vitex agnus-castus* cultivar named 'V07-SC-OP-4'. Data was collected in Griffin, Ga. from three year old plants grown from stem cuttings and growing outdoors. 'V07-SC-OP-4' has not been tested under all possible conditions hence, phenotypic differences may be observed with variations in environmental conditions without any variance in genotype.

Throughout this specification, color names beginning with a small letter signify that the name of that color, as used in common speech, is aptly descriptive. Color names beginning with a capital letter designate values based upon The R.H.S. Colour Chart, 5$^{th}$ edition published by The Royal Horticultural Society (R.H.S.), London, England. This description is from observations of typical three year old plants growing in Griffin, Ga.

Size.—335 cm tall by 395 cm wide, measured at highest and widest point. Size is reflective of habit, i.e., 2' by 3' is rounded to broad-rounded.

Habit: Open, spreading, upright.

Texture: Medium coarse.

Stems:

*First year*.—Color: Grey-Brown N199A. Diameter: 4-5 mm. Pubescence: covered in tiny curved hairs with scattered longer curved hairs. Exfoliation: none. Shape: Round. Pith: Type: Solid. Diameter: 2 mm. Color: White N155D. Odor: strong, spicy, acrid. Internode Length: 7.0 cm.

*Second year*.—Color: Grey-Green 197A. Diameter: 7 mm. Exfoliation: none.

Vegetative buds:

*Arrangement*.—Opposite.

*Type*.—Valvate.

*Size*.—1 mm×1 mm.

*Scale number*.—2.

*Scale color*.—Greyed-Orange 177D.

*Position/disposition*.—45°.

*Number at node*.—2, one on each side.

*Pubescence*.—Scattered short hairs.

*Shape*.—Rounded dome.

Leaf scar:

*Shape*.—Cup shaped.

*Vascular bundle traces*.—3, horizontal and oval.

*Pubescence*.—Dense minute airs around perimeter.

*Position of bud*.—Just above leaf scar.

*Color differentiation*.—Yellow-Green 144A.

*Size*.—2×3 mm.

Trunk or large stems:

*Color(s)*.—Mix of Greyed-White 156A and Greyed-Brown 199D.

*Size stem exfoliation begins on*.—Approximately 5 cm.

*Diameter*.—2.5 to 5.0 cm.

*Texture*.—Usually smooth younger stems, cracking bark by 5.0 cm.

Leaf:

*Color through seasons*.—Emerging dates: mid-April. Upper: Yellow-Green 146A. Lower: Greyed-Green 191B. Summer dates: mid-July. Upper: Green 137A. Lower: Greyed-Green 191B. Fall dates: September. Upper: Yellow-Green 147A. Lower: Greyed-Green 191B.

*Mature size*.—13 cm×14 cm.

*Apex*.—Acute.

*Base*.—Acute.

*Margin*.—Mostly entire.

*Shape*.—Palmate, mostly 7 leaflets. Lobes: None. Sinuses: none.

*Vein color*.—Greyed-Green 194D.

*Pubescence*.—Upper surface has many scattered hairs, with more along the midvein, slightly glandular. Lower leaf is more densely hairy and has a very glandular surface.

*Arrangement on stem*.—Opposite.

*Venation*.—Pinnate.

*Texture*.—Thickness: 0.3 mm. Degree of waxiness of surfaces: slightly waxy on upper surface, completely dull on lower surface.

*Foliage fragrance*.—Mild, spicy.

Petiole:

*Length*.—5.5 to 7.0 cm.

*Shape*.—Round.

*Color*.—Upper Yellow-Green 148C, lower Yellow-Green 145C.

*Pubescence*.—Densely covered in minute curved hairs.

*Diameter*.—2 mm.

Leaflets: Five leaflets were measure on five leaves that had five leaflets per leaf. The leaflets are arranged palmately, going from small to medium to large to medium to small. Mean lengths and widths of each of the five leaflets are as follows: 41.4 mm long, 7 mm wide; 52.4 mm long, 10 mm wide; 66.0 mm long, 12.2 mm wide; 52.4 mm long, 10 mm wide; 34.6 mm long, 7.6 mm wide.

Flower buds:

*Size (l×w)*.—5 mm×3 mm.

*Color*.—Red-Purple 65C.

*Shape*.—Teardrop.

*Pubescence*.—Glandular surface, dense hairs laying flat.

*Time of full maturity (first visible)*.—Early summer.

*Time range for showiness*.—Mid-June through September.

Flower:

*Inflorescence(s)*.—Type: elongated panicle, compound. Size: 14 cm long×3 cm wide (largest sub-panicle in the panicle); individual floret 8 mm long×5 mm wide. Color: At emergence (date): Red-Purple 63C with Red-Purple N66C on anterior lip. Full bloom (date): Red-Purple 63C with Red-Purple N66C on anterior lip. Fading (date): Red-Purple 63C with Red-Purple N66C on anterior lip. Fragrance: mild, sweet, floral. Peduncle: Color: Greyed-Green 193D. Pubescence: short hairs, glandular. Number of individual flowers per inflorescence: 242-588.

*Petal(s)*.—Size: 8 mm×5 mm. Shape: zygomorphic, gamopetalous, bilabiate. Apex: 5 lobes rounded and slightly curled. Base: funnel. Margin: slightly curled. Pubescence: scattered hairs on edges, thickly tufted inside at base of pistil. Texture: inside glabrous, outside scattered glandular. Color at peak of bloom: Upper surface: Red-Purple 63C with Red-Purple N66C on anterior lip. Lower surface: Red-Purple 65C. Pedicels: Color (R.H.S.): Greyed-Green 193A. Pubescence: covered in short hairs. Length: 1-2 mm.

*Sepal(s)*.—Size (l×w): 3.5 mm×2 mm. Shape: united, slightly lobed. Apex: slightly lobed. Base: united, short tubular. Margin: smooth. Pubescence: glandular, tomentose — short hairs. Texture: hoary. Color at peak of bloom: Upper surface: Greyed-Green 193A with Purple-Violet N81C. Lower surfaces: Yellow-Green 144C with Violet-Blue 93C.

*Male reproductive structures*.—Number: 4. Anther: Size (l×w): 1 mm×0.5 mm. Color: Violet 86B. Filament: Size (l×w): 5 mm×0.5 mm. Color: White N155A. Pollen color: Green-White 157D. Pubescence: thick tufted at base.

*Female reproductive structures*.—Pistil: Shape: tubular, bifid. Size (l×w): 5 mm×0.5 mm. Position (superior, inferior, etc.): superior. Color (RHS): Purple-Violet N80C. Pubescence: thickly tufted hairs at base. Stigma: Shape: round, bifid. Color (RHS): White 155C. Pubescence: none. Style: Length: 6 mm. Shape: tubular, forked at stigma (bifid). Color (RHS): Violet 84A. Pubescence: glabrous, tufted at base. Ovary: Shape: round. Number: 1. Pubescence: scattered short hairs, numerous glands present on surface.

Fruit:

*Type*.—Drupe-like.

*Size (l×w)*.—4 mm×3 mm.

*Color(s) during ripening*.—Early (date): Yellow-Green 154B. Mid (date): Greyed-Orange 175B. Late (date): Brown 200A.

*Shape*.—Globular.

*Number per infructescence*.—1.

*Pubescence*.—Few scattered hairs.

*Number of carpels*.—2.

*Persistence (effective period)*.—Mid to late summer through fall into winter.

Seed:

*Shape*.—Globular.

*Size*.—3.5 mm×2.5 mm, oval.

*Color*.—Brown 200A when fully ripe.

*Number per locule per ovary per fruit*.—1.

*Germination capacity*.—Not tested.

*Pubescence*.—Scattered minute hairs.

Disease and pest resistance: Not observed to date.

Plant hardiness: The new variety has been grown in USDA hardiness zone 8a and has also been evaluated growing successfully in USDA hardiness zone 6b.

What is claimed is:

1. A new and distinct cultivar of the *Vitex agnus-castus* plant named 'V07-SC-OP-4' substantially as illustrated and described herein.

* * * * *

'V07-SC-OP-4'

'Salinas Pink'

'V07-SC-OP-4'

'Salinas Pink'

'V07-SC-OP-4'

'Salinas Pink'

'V07-SC-OP-4'